US011028132B1

(12) United States Patent
Rosen (10) Patent No.: US 11,028,132 B1
(45) Date of Patent: Jun. 8, 2021

(54) HALF-LIFE OPTIMIZED LINKER COMPOSITION

(71) Applicant: Yitzhak Rosen, Highland Park, NJ (US)

(72) Inventor: Yitzhak Rosen, Highland Park, NJ (US)

( * ) Notice: Subject to any disclaimer, the term of this patent is extended or adjusted under 35 U.S.C. 154(b) by 0 days.

(21) Appl. No.: 16/938,707

(22) Filed: Jul. 24, 2020

Related U.S. Application Data (60) Provisional application No. 63/006,357, filed on Apr. 7, 2020.

(51) Int. Cl.
| | | |
|---|---|---|
| *C07K 14/165* | (2006.01) | |
| *A61K 38/00* | (2006.01) | |
| *C12N 7/00* | (2006.01) | |
| *C07K 14/005* | (2006.01) | |

(52) U.S. Cl.
CPC .............. *C07K 14/005* (2013.01); *C12N 7/00* (2013.01); *A61K 38/00* (2013.01); *C07K 14/165* (2013.01); *C07K 2319/30* (2013.01); *C07K 2319/33* (2013.01); *C12N 2770/20022* (2013.01); *C12N 2770/20033* (2013.01)

(58) Field of Classification Search
CPC .......... A61K 2300/00; A61K 2039/505; A61K 38/1774; A61K 39/395; A61K 47/65; A61K 9/5169; A61K 38/00; C07K 16/00; C07K 2319/31; C07K 14/70535; C07K 16/10; C07K 16/283; C07K 2317/22; C07K 2317/53; C07K 2317/569; C07K 2317/622; C07K 2317/76; C07K 2317/94; C07K 2319/00; C12N 9/003; G01N 33/56938; C12Y 301/06012; C12P 19/18; A61P 31/14
See application file for complete search history.

(56) References Cited

U.S. PATENT DOCUMENTS

| | | | |
|---|---|---|---|
| 8,524,214 B2 | 9/2013 | Yurkovetskiy et al. | |
| 9,475,857 B2 | 10/2016 | Glass et al. | |
| 10,150,800 B2 | 12/2018 | Roschke et al. | |
| 2006/0240515 A1* | 10/2006 | Dimitrov | A61K 39/215 |
| | | | 435/69.1 |
| 2017/0037102 A1 | 2/2017 | Greve | |

FOREIGN PATENT DOCUMENTS

| | | |
|---|---|---|
| AU | 2010226392 | 10/2011 |
| CA | 2739615 | 4/2010 |

OTHER PUBLICATIONS

Capon et al. Nature, 1989, vol. 337, pp. 525-531.*
Strohl W. BioDrugs, 2015, vol. 29, pp. 215-239.*
Redpath et al. Human Immunology, 1998, vol. 59, Issue 11, pp. 720-727.*
Griffin et al. Journal of Immunological Methods 2014, vol. 405, pp. 35-46.*
Wu et al. (Nature 2020, vol. 579 (7798): 265-269).*

* cited by examiner

*Primary Examiner* — Bao Q Li
(74) *Attorney, Agent, or Firm* — Patent Ventures, LLC (57) ABSTRACT

Coronavirus disease 2019 (COVID-19 or COVID-2) is an infectious disease caused by severe acute respiratory syndrome coronavirus 2 (SARS-CoV-2). Common symptoms include fever, cough, and shortness of breath. The virus is mainly spread during close contact and via respiratory droplets produced when people cough or sneeze. Respiratory droplets may be produced during breathing but the virus is not generally airborne. A half-life optimized fusion composition linked by a Half-Life Optimizing (H-Lo) linker comprising of a receptor binding domain (RBD), a half-life extending domain (LED), wherein the LED is any one of a monoclonal antibody, single domain antibody, nanobody, antibody fragment, or combination thereof and the H-Lo linker with an X+7 amino acid length fusing the RBD C-terminus with the LED N-terminus (RBD-LED fusion) is discussed in the invention.

15 Claims, 6 Drawing Sheets

Specification includes a Sequence Listing.

MFVFLVLLPLVSSQCVNLTRTQLPPAYTNSFTRGVYYPDKVFRSSVLHSTQDLFLPFFSNVTWFHAI
HVSGTNGTKRFDNPVLPFNDGVYFASTEKSNIIRGWIFGTTLDSKTQSLLIVNNATNVVIKVCEFQF
CNDPFLGVYYHKNNKSWMESEFRVYSSANNCTFEYVSQPFLMDLEGKQGNFKNLREFVFKNIDGY
FKIYSKHTPINLVRDLPQGFSALEPLVDLPIGINITRFQTLLAL

Fig. 5

Remove one VHH from humanized Camelid IgG2 Fc → Fuse SARS-CoV-2 RBD to humanized Camelid IgG2 Fc via linker → Utilize RBD to outcompete S protein and encourage broad neutralizing Abs → Intravenously or subcutaneous delivery → Virus RBD binds to an ACE 2 as a trimer

Fig. 6

SEQUENCE LISTING

```
<160> NUMBER OF SEQ ID NOS: 1

<210> SEQ ID NO 1
<211> LENGTH: 7
<212> TYPE: PRT
<213> ORGANISM: Betacoronavirus Severe acute respiratory syndrome
      related coronavirus

<400> SEQUENCE: 1

Thr Glu Ser Ile Val Arg Phe
1               5
```

HALF-LIFE OPTIMIZED LINKER COMPOSITION

INCORPORATION BY REFERENCE

The ASCII text file is named "SequenceASCIItextfile11-13-2020" and is 11393 bytes. The sequence is a part of FIG. 4.

BACKGROUND

Coronavirus disease 2019 (COVID-19 or COVID-2) is an infectious disease caused by severe acute respiratory syndrome coronavirus 2 (SARS-CoV-2). Common symptoms include fever, cough, and shortness of breath. Other symptoms may include muscle pain, sputum production, diarrhea, sore throat, loss of smell, and abdominal pain. While the majority of cases result in mild symptoms, some progress to pneumonia and multi-organ failure.

The virus is mainly spread during close contact and via respiratory droplets produced when people cough or sneeze. Respiratory droplets may be produced during breathing but the virus is not generally airborne. People may also contract COVID-19 by touching a contaminated surface and then their face. It is most contagious when people are symptomatic, although spread may be possible before symptoms appear. The virus can survive on surfaces up to 72 hours. Time from exposure to onset of symptoms is generally between two and fourteen days, with an average of five days. The standard method of diagnosis is by reverse transcription polymerase chain reaction (rRT-PCR) from a nasopharyngeal swab. The infection can be diagnosed from a combination of symptoms, risk factors and a chest CT scan showing features of pneumonia. COVID-2 virus has devasting global pandemic that has cost thousands of lives and infected many thousands more. There are ongoing efforts to develop vaccines and treatment.

Like other coronaviruses, SARS-CoV-2 has four structural proteins, known as the N protein holds the RNA genome, and the S, E, and M proteins together create the viral envelope. The spike protein, which has been imaged at the atomic level using cryogenic electron microscopy, is the protein responsible for allowing the virus to attach to the membrane of a host cell. Each SARS-CoV-2 virion is approximately 50-200 nanometres in diameter.

The spike protein of the virus SARS-CoV-2 has sufficient affinity to the angiotensin converting enzyme 2 (ACE2) receptors of human cells to use them as a mechanism of cell entry. Studies have shown that SARS-CoV-2 has a higher affinity to human ACE2 than the original SARS virus strain. SARS-CoV-2 may also use basigin to gain cell entry.

Initial spike protein priming by transmembrane protease, serine 2 (TMPRSS2) is essential for entry of SARS-CoV-2. After a SARS-CoV-2 virion attaches to a target cell, the cell's protease TMPRSS2 cuts open the spike protein of the virus, exposing a fusion peptide. The virion then releases RNA into the cell, forcing the cell to produce copies of the virus that are disseminated to infect more cells. SARS-CoV-2 produces at least three virulence factors that promote shedding of new virions from host cells and inhibit immune response.

Previous studies have shown the use of neutralizing fusion antibodies to fight against viruses like SARS-CoV and MERS-CoV. As a vital factor of recombinant fusion proteins, linkers have shown increasing importance in the construction of stable, bioactive fusion proteins. The general properties of linkers derived from naturally-occurring multi-domain proteins can be considered as the foundation in linker design. Empirical linkers designed by researchers are generally classified into 3 categories according to their structures: flexible linkers, rigid linkers, and in vivo cleavable linkers.

Besides the basic role in linking the functional domains together (as in flexible and rigid linkers) or releasing free functional domain in vivo (as in in vivo cleavable linkers), linkers may offer many other advantages for the production of fusion proteins, such as improving biological activity, increase half-life, increasing expression yield, and achieving desirable pharmacokinetic profiles. The successful construction of a recombinant fusion protein requires two indispensable elements: the component proteins and the linkers. Direct fusion of functional domains without a linker may lead to many undesirable outcomes, including misfolding of the fusion proteins, low yield in protein production, or impaired bioactivity. Therefore, the selection or rational design of a linker to join fusion protein domains is extremely important.

SUMMARY

In accordance with the present invention, a half-life optimized fusion composition linked by a Half-Life Optimizing (H-Lo) linker comprising of a receptor binding domain (RBD), a half-life extending domain (LED), wherein the LED is any one of a monoclonal antibody, single domain antibody, nanobody, antibody fragment, or combination thereof and the H-Lo linker with an X+7 amino acid length fusing the RBD C-terminus with the LED N-terminus (RBD-LED fusion), wherein a value for X varies depending on at least one of a structural conformation of an interacted RBD-LED fusion or a structural conformation of a target site of the RBD-LED fusion. Furthermore, the RBD is of at least one of S (spike), E (envelope), M (membrane), and N (nucleocapsid) proteins and further yet, the RBD of the S (Spike) protein further comprises of a 51 and S2 subunit.

In addition, in an embodiment of the invention, the RBD-LED fusion is recombinantly engineered by at least one of repertoire cloning, CRISPR/Cas9, single B cell culture, single cell amplification from B cell populations, single plasma cell interrogation or phage display/yeast display technologies.

Additionally, in an embodiment of the present invention, the H-Lo linker is at least between 2 and 31 amino acids in length and further comprises at least one of Glycine, Serine or Threonine, or a combination thereof depending on at least one of the structural conformations of the RBD-LED fusion or RBD-LED target site. Further yet, in an embodiment of the invention, the value for X further depends on the construction of a functional chimeric protein and is at least in an ideal range of 5-11 amino acids. Additionally, the RBD is of SARS-CoV-2 and the LED is of a camelid fusion antibody. Additionally, an amino acid value range for X is half-life optimized for fusing an ACE-2 receptor with an RBD-Camelid Fc fragment (LED). In addition, in an embodiment of the invention, the ACE-2 RBD-Camelid Fc (LED) is half-life optimized for prolonged targeting of an ACE2 receptor for antagonist binding. Further yet, wherein the ACE-2 RBD-Camelid Fc LED fusion comprises a H-Lo linker of a specific gene and/or amino acid sequence. The H-Lo linker further comprises of a spacer having an amino acid sequence comprising of TESIVRF. Further yet, the H-Lo is bound to the Camelid Fc at one terminal and the RBD at the other terminus.

In another embodiment of the invention, the ACE-2 receptor antagonism results in a failure of a COVID-2 spike protein binding and a subsequent COVID-2 viral infection. Further yet, the ACE-2 RBD-Camelid Fc LED fusion with H-Lo linker is delivered via at least one of, but not limited to, subcutaneously, nasally, orally or intravenously.

In accordance to the present invention, in an embodiment, a half-life optimized Receptor Binding Domain (RBD) and half-Life Extending Domain (LED) fusion composition linked by a Half-Life Optimizing (H-LO) linker comprising of a RBD, wherein the RBD is specific to the ACE-2, a LED, wherein the LED is a Camelid monoclonal Fc Fragment and a H-Lo linker with an X+7 amino acid length fusing the RBD C-terminus with the LED N-terminus (RBD-LED fusion), wherein a value for X varies depending on at least one of a structural conformation of an interacted RBD-LED fusion or a structural conformation of a target site of the RBD-LED fusion. In addition, the amino acid value range for X is half-life optimized for a proper fusion of an ACE-2 receptor with a RBD-Camelid Fc fragment (LED). Further yet, the ACE-2 RBD-Camelid Fc (LED) is half-life optimized for prolonged targeting of an ACE2 receptor for antagonist binding. Additionally, in an embodiment of the ACE-2 RBD-Camelid Fc LED fusion comprises of a H-Lo linker of a specific gene and/or amino acid sequence.

In addition in an embodiment of the invention, a method of composing an RBD-LED fusion with H-Lo linker, comprising the steps of fusing a H-Lo linker with an X+7 amino acid length to a receptor binding domain (RBD) C-terminus with a half-life extending domain (LED) N-terminus (RBD-LED fusion), wherein a value for X varies depending on at least one of a structural conformation of an interacted RBD-LED fusion or a structural conformation of a target site of said RBD-LED fusion.

Additionally in an embodiment of the invention, a method of composing an ACE-2 RBD-Camelid Fc fragment LED fusion with H-Lo linker comprising the steps of fusing a H-Lo linker with an X+7 amino acid length to a receptor binding domain (RBD) C-terminus of the ACE-2 receptor with a half-life extending domain (LED) N-terminus (RBD-LED fusion) of the Camelid Fc fusion protein, wherein a value for said x varies depending on at least one of a structural conformation of an interacted RBD-LED fusion or a structural conformation of a target site of said RBD-LED fusion.

In addition the present invention suggests a method of antagonizing the ACE-2 receptor for repression of COVID-2 viral activation comprising the steps of fusing a H-Lo linker with an X amino acid length to a receptor binding domain (RBD) C-terminus of the ACE-2 receptor with a half-life extending domain (LED) N-terminus (RBD-LED fusion) of the Camelid Fc fusion protein, wherein a value for said X varies depending on at least one of a structural conformation of an interacted RBD-LED fusion or a structural conformation of a target site of said RBD-LED fusion.

Additionally, the present invention teaches an isolated neutralizing monoclonal antibody composition for a SARS-Cov-2 comprising of, a receptor binding domain (RBD) of the SARS-Cov-2 spike protein, a fusion antibody wherein VHH fragment is replaced with the RBD of SARS-CoV-2 on a humanized IgG2 Fc wherein linking of the RBD of the SARS-Cov-2 spike protein to the fusion antibody via FcRn mediated cytosis increases half-life to promote binding to a membrane bound ACE2 receptor.

Further, wherein the fusion antibody is a camelid antibody IgG 2 (Camelid Fc). In addition, the neutralizing monoclonal antibody comprises of a linker with an X plus 7 amino acid preceding the RBD of the SARS-Cov-2 sequence for optimal functioning and folding of the RBD wherein the value of X is variable depending on the structural conformity of the RBD to promote appropriate fusion with the fusion antibody. The value of X in the linker maybe optimized to increase half-life to promote fusion of an ACE2 receptor with the SARS-CoV-2-RBD-Camelid Fc antibody. Additionally, the Camelid Fc and SARS-Cov-2 RBD fusion is optimized for an extended targeting of an ACE2 receptor for an antagonist binding.

In addition, the camelid antibody fusion with humanized IgG2 Fc is recombinantly engineered by at least of repertoire cloning, CRISPR/Cas9, single B cell culture, single cell amplification from B cell populations, single plasma cell interrogation or phage display/yeast display technologies.

Furthermore, an isolated neutralizing monoclonal antibody composition for a SARS-Cov-2, comprising of a receptor binding domain (RBD) of the SARS-Cov-2 spike protein, a fusion antibody wherein VHH fragment is replaced with an RBD of SARS-CoV-2 on a humanized IgG2 Fc wherein linking of the RBD of the SARS-Cov-2 spike protein to the fusion antibody is via FcRn mediated cytosis that increases half-life to promote binding to a membrane bound ACE2 receptor.

Other devices, apparatus, and/or products according to embodiments will be or will become apparent to one of ordinary skill in the art upon review of the following drawing and further description. It is intended that all such additional devices, apparatus, and/or products be included within this description, be within the scope of the present invention, and be protected by the accompanying claims.

DETAILED DESCRIPTION

The following is a discussion and description of preferred specific embodiments of the half-life optimized fusion composition linked by a Half-Life Optimizing (H-Lo) linker as claimed, such being made with reference to drawings, and in particular to FIGS. 1 to 6 thereof, whereupon the same reference numerals are used to indicate the same or similar parts and/or structure. Such discussion and description is to illustrate and not to unduly limit the scope of the invention.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

Figure 1:
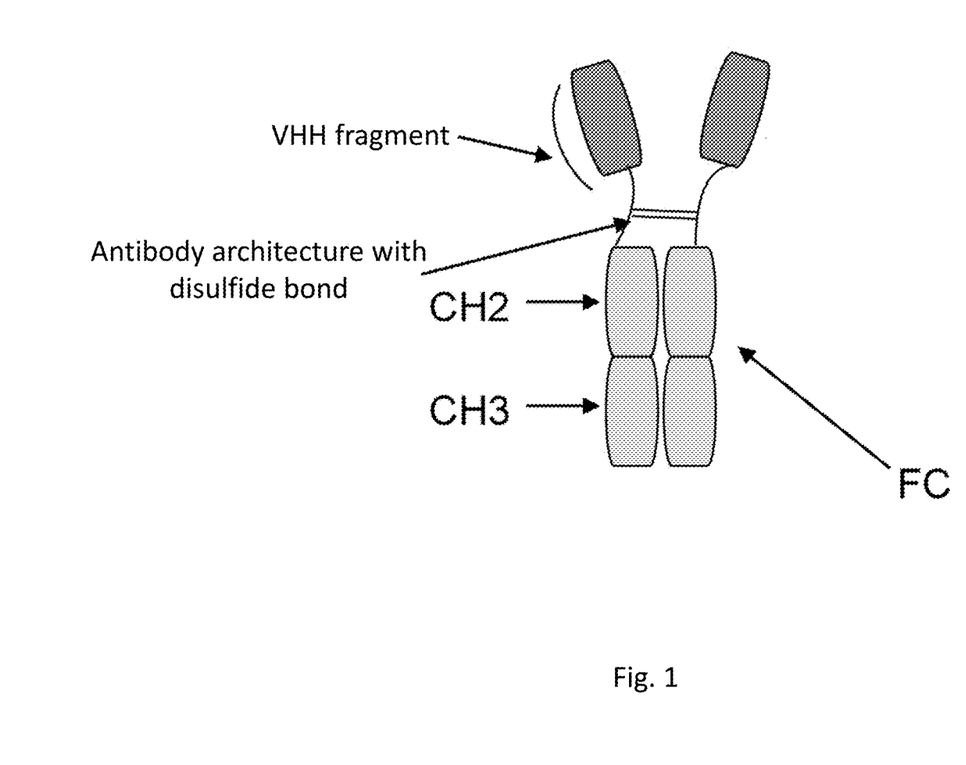
FIG. 1 shows a Camelid antibody architecture, according to an aspect of the invention.

FIG. 1 represents a Camelid antibody architecture having humanized IgG2 Fc fragment with two VHH fragments. Fc-fusion proteins are bioengineered polypeptides that join the crystallizable fragment (Fc) domain of an antibody with another biologically active protein domain or peptide to generate a molecule with unique structure-function properties and significant therapeutic potential. The gamma immunoglobulin (IgG) isotype is often used as the basis for generating Fc-fusion proteins because of favorable characteristics such as recruitment of effector function and increased plasma half-life. Given the range of proteins that can be used as fusion partners, Fc-fusion proteins have numerous biological and pharmaceutical applications, which has launched Fc-fusion proteins into the forefront of drug development.

Figure 2:
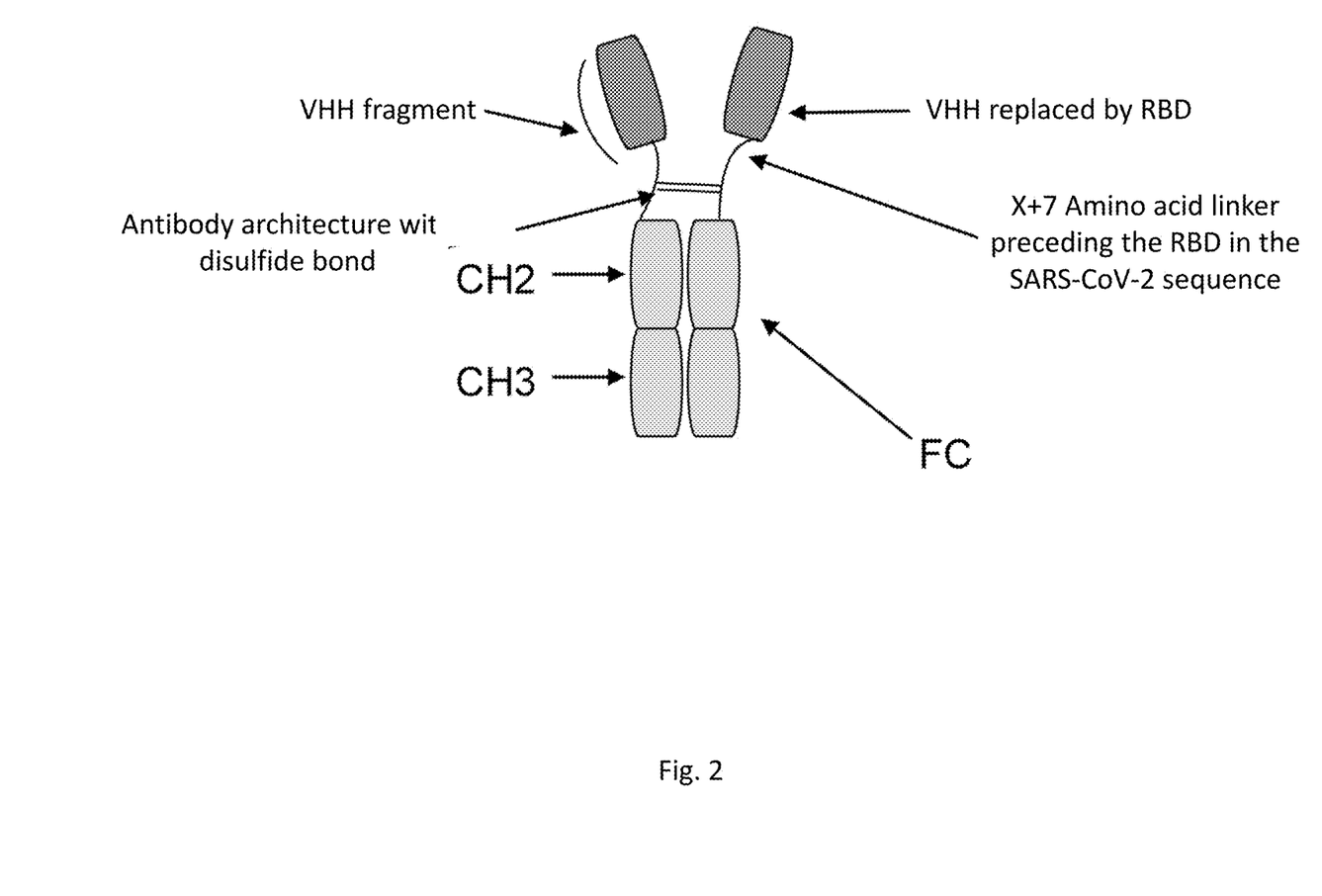
FIG. 2 shows a version of a Camelid antibody architecture, according to an aspect of the invention.

As referred in FIG. 1 and FIG. 2, in a preferred embodiment of the invention, a half-life optimized fusion composition linked by a Half-Life Optimizing (H-Lo) linker, composition comprising of, a receptor binding domain (RBD), a half-life extending domain (LED), wherein the LED is any one of a monoclonal antibody, single domain antibody, nanobody, antibody fragment, or combination thereof and the H-Lo linker with an X+7 amino acids length fusing the RBD C-terminus with the LED N-terminus (RBD-LED fusion), wherein a value for X varies depending on at least one of a structural conformation of an interacted RBD-LED fusion or a structural conformation of a target site of the RBD-LED fusion.

Further yet, in an embodiment the RBD is of at least one of S (spike), E (envelope), M (membrane), and N (nucleocapsid) proteins and the RBD of the S (Spike) protein further comprises of S1 and S2 subunits. Additionally, in an embodiment of the invention, the RBD-LED fusion is recombinantly engineered by at least one of repertoire cloning, CRISPR/Cas9, single B cell culture, single cell amplification from B cell populations, single plasma cell interrogation or phage display/yeast display technologies.

In addition, the H-Lo linker is at least between 2 and 31 amino acids in length. The H-Lo linker further comprises at least one of Glycine, Serine or Threonine, or a combination thereof depending on at least one of the structural conformations of the RBD-LED fusion or RBD-LED target site. Additionally, the value for X further depends on the of a functional chimeric protein and is at least in an ideal range of 5-11 amino acids.

In a preferred embodiment, the RBD is of SARS-CoV-2 and the LED is of a Camelid fusion antibody. Further yet, an amino acid value range for X is half-life optimized for fusing of an ACE-2 receptor with an RBD-Camelid Fc fragment (LED). Additionally, in an embodiment of the invention, ACE-2 RBD-Camelid Fc (LED) is half-life optimized for prolonged targeting of an ACE2 receptor for antagonist binding. Moreover, the ACE-2 RBD-Camelid Fc LED fusion comprises a H-Lo linker of a specific gene and/or amino acid sequence. In a preferred embodiment, the H-Lo linker further comprises of a spacer with an amino acid sequence comprising of TESIVRF (Seq ID NO 2). Further yet, the ACE-2 receptor antagonism results in a failure of a COVID-2 spike protein binding and a subsequent COVID-2 viral infection. Further yet in an embodiment, the linker may or may not contain a spacer. Additionally, the spacer may be further comprised of a varying amino acid sequence. The spacer may or may not be linked to the linker. The link between the spacer and linker may vary. The spacer is ideally 7 amino acids in length, however the length of the amino acid sequence may vary.

In addition, the ACE-2 RBD-Camelid Fc LED fusion with H-Lo linker is delivered via at least one of, but not limited to, subcutaneously, nasally, orally or intravenously.

In another preferred embodiment of the invention, an isolated neutralizing monoclonal antibody comprising of a receptor binding domain (RBD) of the SARS-Cov-2 spike protein, a fusion antibody wherein a VHH fragment is replaced with the RBD on a humanized IgG2 Fc, wherein linking of the RBD of the SARS-Cov-2 spike protein to the fusion antibody is via FcRn mediated cytosis that increases half-life to promote binding to a membrane bound ACE2 receptor. Further yet, the fusion antibody is a camelid antibody IgG 2 (Camelid Fc). In addition, in a preferred embodiment of the invention, a linker with an X plus 7 amino acid preceding the RBD of the SARS-Cov-2 sequence is attached for optimal functioning and folding of the RBD wherein the value of X is variable depending on the structural conformity of the RBD to promote appropriate fusion with the fusion antibody.

In yet another alternate embodiment, in order to improve expression levels, solubility, folding, purification, and detection of recombinant proteins, a very common strategy is the fusion of peptides or proteins also known as "tags," to the target protein. Because these tags are entities with known sequences and well-characterized physicochemical properties, they are an essential tool that facilitates expression and purification of recombinant proteins. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag, Spot-tag, T7-tag and NE-tag. These tags are particularly useful in antibody purification. A plurality of peptide epitope tags include 6X His (also known as His-tag or hexahistidine tag), FLAG, HA, Myc, and V5. Popular protein epitope tags are GFP (green fluorescent protein), GST (glutathione-S-transferase), β-GAL (β-galactosidase), Luciferase, MBP (Maltose Binding Protein), RFP (Red Fluorescence Protein), and VSV-G (Vesicular Stomatitis Virus Glycoprotein).

Alternatively, in an embodiment of the invention, a linker may or may not need the additional 7 amino acid spacer preceding the RBD of the SARS-Cov-2 sequence for optimal functioning and folding of the RBD. Further yet, the amino acid sequence of the spacer may vary for optimal functioning and folding of the RBD. In yet another alternate embodiment, Camelid single-domain fragments (nanobodies) may be used to bring about conformational change to promote fusion. Alternatively, fusion proteins may be engineered with or without the use of linkers.

In another embodiment of the invention, nanoparticles may be used to engineer fusion particles for efficient cell targeting using linker-free methods based on catechol reactions. To take advantage of unique properties of nanoscale materials and structures, the size, shape and/or surface chemistry of nanoparticles will be optimized, allowing their functionalities to be tailored for different biomedical applications. Various nanoparticles e.g. Iron oxide nanoparticles, PEG (polyethylene glycol) nano particles, titanium dioxide, PVP-coated iron oxide, gold coated, Polystyrene etc. with or without a linker may be used to create novel functional approaches for disease diagnostics and therapeutics of various diseases. Additionally, in an embodiment, the density of ligands and linker length may vary in nanoparticle-receptor interactions for optimal interaction and fusion of various proteins.

In yet another preferred embodiment of the invention, the value of X in the linker maybe optimized to increase half-life to promote fusion of an ACE2 RBD-Camelid Fc antibody. Additionally, the Camelid Fc and SARS-Cov-2 RBD fusion is optimized for an extended targeting of an ACE2 receptor for an antagonist binding. In addition, a number or sequence of amino acids on the linker varies to ensure a proper folding of the RBD. Preferably, in an embodiment of the invention, the sequence of amino acid on a spacer preceding the linker is TESIVRF (SEQ ID NO: 2).

Furthermore, the RBD is of at least one of S (spike), E (envelope), M (membrane), and N (nucleocapsid) proteins and the RBD of the S (spike) protein comprises of a 51 and a S2 subunit.

In addition, the RBD-LED fusion is recombinantly engineered by at least one of repertoire cloning, CRISPR/Cas9, single B cell culture, single cell amplification from B cell populations, single plasma cell interrogation or phage display/yeast display technologies. Further yet, an optimal pharmaceutical composition comprising of an effective amount of the antibody and a pharmaceutically acceptable carrier for delivery via at least one of, but not limited to, subcutaneously, nasally, orally or intravenously.

Figure 3:
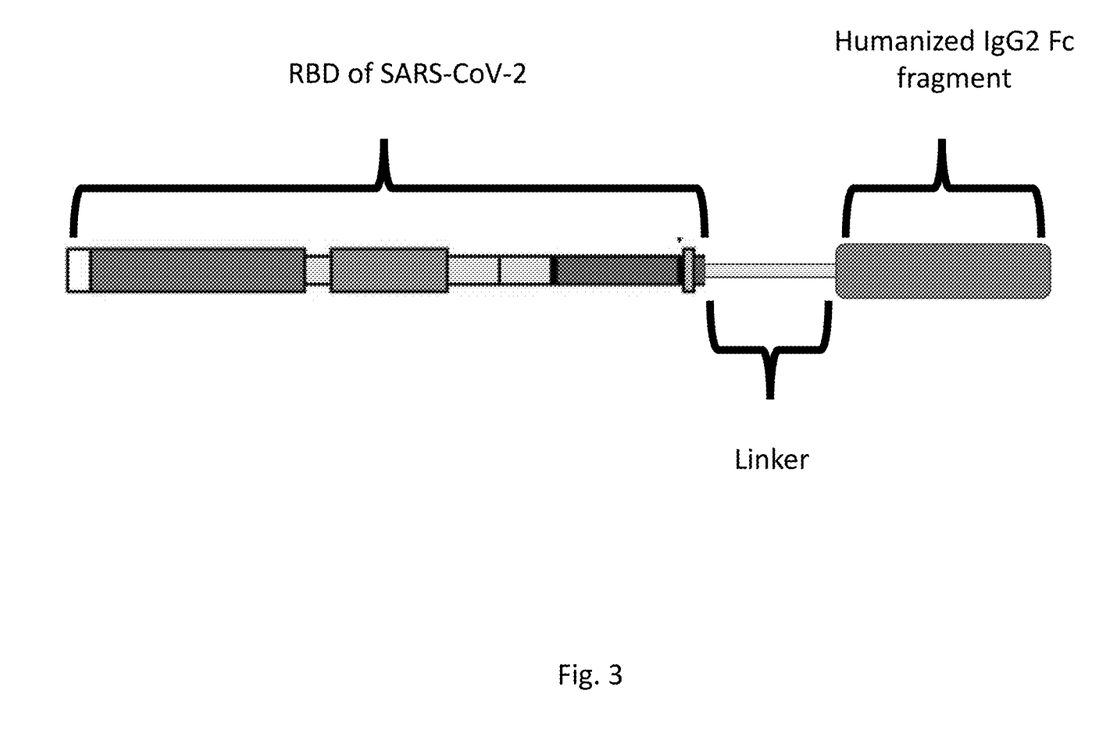
FIG. 3 shows a block diagram, according to an aspect of the invention.
Figure 4:
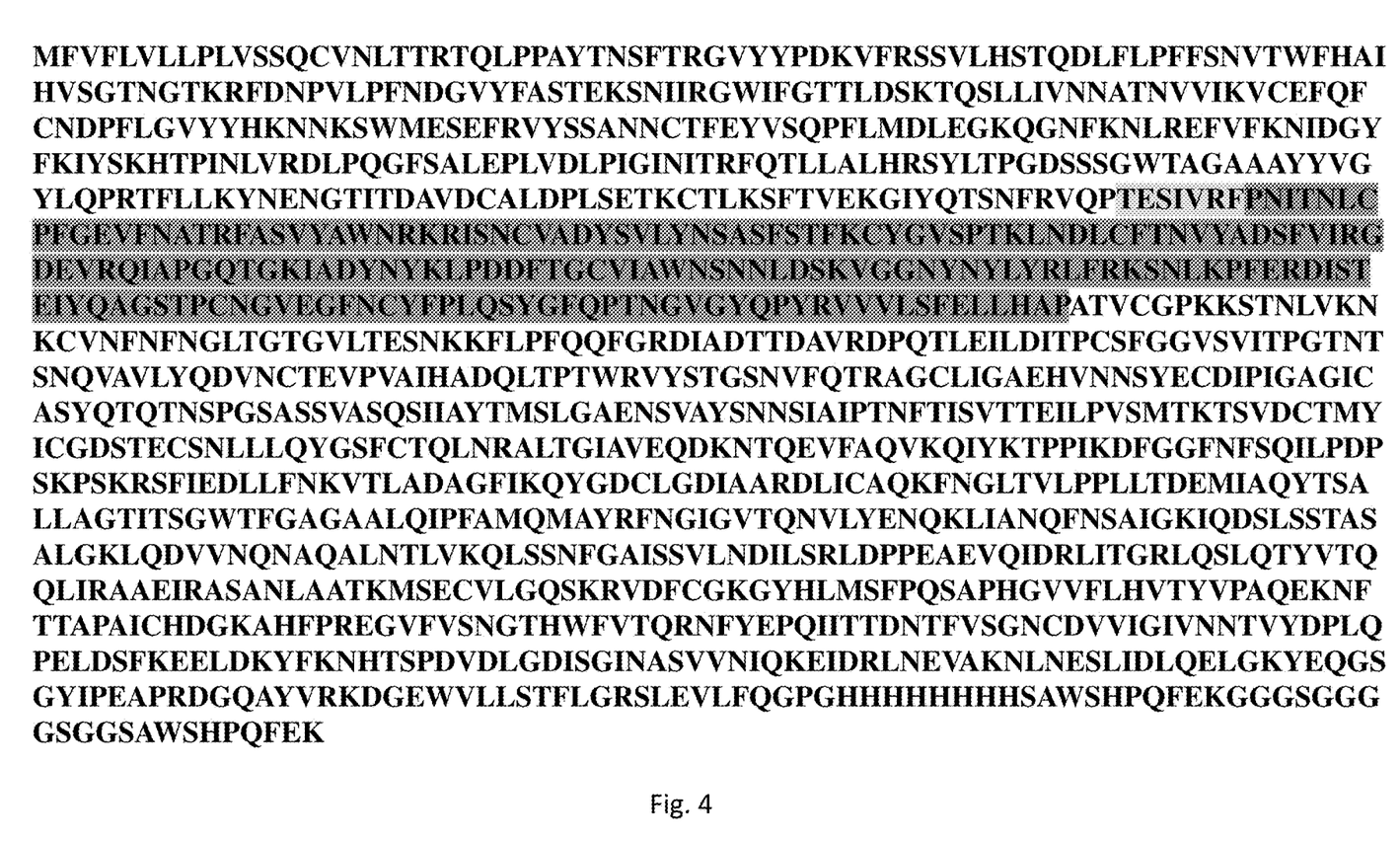
FIG. 4 shows COVID-19 S (Spike) protein sequence (SEQ ID NO: 1 and SEQ ID NO: 2).

As shown in FIG. 3 and FIG. 4, in a preferred embodiment of the invention, a half-life optimized Receptor Binding Domain (RBD) and the half-Life Extending Domain (LED) fusion composition linked by a Half-Life Optimizing (H-LO) linker comprising of a RBD, wherein the RBD is specific to the ACE-2, a LED, wherein the LED is a Camelid monoclonal Fc Fragment and a H-Lo linker with an X+7 amino acid length fusing with the RBD C-terminus with the LED N-terminus (RBD-LED fusion), wherein a value for X varies depending on at least one of a structural conformation of an interacted RBD-LED fusion or a structural conformation of a target site of the RBD-LED fusion.

In a preferred embodiment, the RBD is of SARS-CoV-2 and the LED is of a Camelid fusion antibody. Further yet, an amino acid value range for X is half-life optimized for fusing of an ACE-2 receptor with an RBD-Camelid Fc fragment (LED). Additionally, ACE-2 RBD-Camelid Fc (LED) is half-life optimized for prolonged targeting of an ACE2 receptor for antagonist binding. Moreover, the ACE-2 RBD-Camelid Fc LED fusion comprises a H-Lo linker of a specific gene and/or amino acid sequence. In a preferred embodiment, the H-Lo further comprises of a spacer which has the amino acid sequence comprising of TESIVRF (SEQ ID NO: 2). In addition, the ACE-2 receptor antagonism results in a failure of the SARS-CoV-2 spike protein binding and subsequent SARS-CoV-2 viral infection.

Further yet, an optimal pharmaceutical composition comprising of an effective amount of the antibody and a pharmaceutically acceptable carrier for delivery via at least one of, but not limited to, subcutaneously, nasally, orally or intravenously.

In an alternative embodiment of the invention, fusion proteins are also designed via tandem fusion between proteins, domain insertion or post-translation conjugation using ribosomal translation of the proteins of interest. Additionally, varying types of linkers may be used e.g. flexible linkers, rigid linkers and in vivo cleavable linkers.

Figure 5:
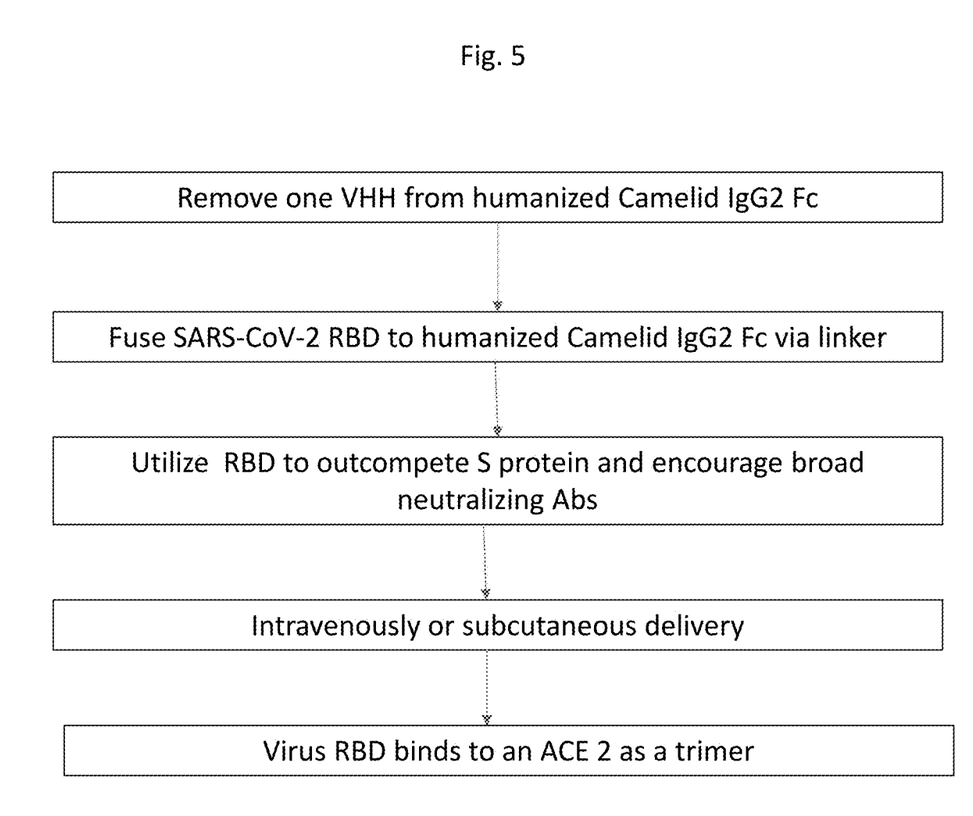
FIG. 5 shows a method flow, according to an aspect of the invention.

Now in reference to FIG. 5, A method of composing an RBD-LED fusion with H-Lo linker comprising the step of, fusing a H-Lo linker with an X+7 amino acid length to a receptor binding domain (RBD) C-terminus with a half-life extending domain (LED) N-terminus (RBD-LED fusion), wherein a value for said X varies depending on at least one of a structural conformation of an interacted RBD-LED fusion or a structural conformation of a target site of the RBD-LED fusion. Further yet, in an embodiment the RBD is of at least one of S (spike), E (envelope), M (membrane), and N (nucleocapsid) proteins and the RBD of the S (Spike) protein further comprises of 51 and S2 subunits. Additionally, the amino acid value range for X is half-life optimized for fusing of an ACE-2 receptor with a RBD-Camelid Fc fragment (LED).

In addition, in a preferred embodiment of the invention, a linker with an X plus 7 amino acid preceding the RBD of the SARS-Cov-2 sequence for optimal functioning and folding of the RBD wherein the value of X is variable depending on the structural conformity of the RBD to promote appropriate fusion with the fusion antibody.

In a preferred embodiment, the H-Lo further comprises of a spacer with an amino acid sequence comprising of TESIVRF (SEQ ID NO: 2). Additionally, the amino acid sequence of the spacer may vary. Alternatively, the H-Lo linker may not have a spacer. Further yet, the ACE-2 receptor antagonism results in a failure of a COVID-2 spike protein binding and a subsequent COVID-2 viral infection. In addition, the ACE-2 RBD-Camelid Fc LED fusion with H-Lo linker is delivered via at least one of, but not limited to, subcutaneously, nasally, orally or intravenously.

Figure 6:
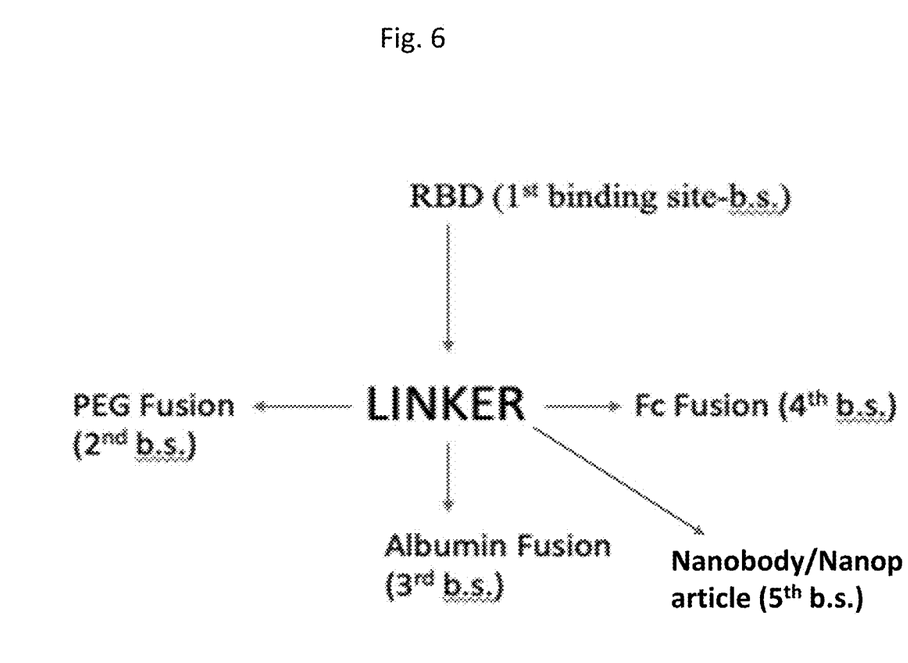
FIG. 6 shows a linker, according to an aspect of the invention.

With reference to FIG. 6, in an embodiment a half-life optimized linker (H-Lo) composition comprising of a site configured to bind to a RBD, a site coupled to a PEG, a third site coupled to a fatty acid chain configured to bind an Albumin, a fourth site with a 'X+7' chain, wherein X is a value of amino acid length representing a hinge and wherein 7 is an amino acid length representing a spacer, wherein the 'X+7' is configured to bind a Fc fragment and a fifth site wherein a nanoparticle is coated with at least one of cationic, anionic or zwitterionic ligand.

In addition, in an embodiment of the invention, wherein the second site is coupled to a PEG through a thiol group wherein the PEG is coupled to an N-terminal amino group of a lysine. Further yet, the PEG alters a hydrocarbon radius of the RBD to above a renal clearance threshold, thereby inhibiting metabolic removal by excretion and extending half-life of the RBD. Additionally, in an embodiment the third site is coupled to a fatty acid chain configured to bind Albumin, thereby extending half-life of the RBD via FcRn-mediated endocytosis. Moreover, in an embodiment of the invention any one the sites are overlapping. Additionally, in an embodiment, the half-life optimized linker (H-Lo) further comprises of a fifth site configured for facilitating encapsulation by a carrier of the linker with RBD.

In an alternative embodiment, the half-life optimized linker configured to RBD may further bind to at least one of or a combination thereof, albumin, PEG, Fc fragment bound to X+7 or a nanoparticle coated with appropriate ligand. Further yet, in an embodiment, the half-life (H-Lo) optimized linker may first be configured to an appropriate RBD and the RBD may dictate further binding to at least one of or a combination thereof, albumin, PEG, Fc fragment bound to X+7 or a nanoparticle coated with appropriate ligand. Further yet, in an embodiment, the half-life optimized linker configured to the RBD further bound to the Fc fragment may not bind to the endogenous albumin.

In a preferred embodiment of the invention, a half-life optimized linker (H-Lo) composition comprising of at least one of a site configured to bind to a RBD, a site coupled to a PEG, a site coupled to a fatty acid chain configured to bind an Albumin, a site with a 'X+7' chain, wherein X is a value of amino acid length representing a hinge and wherein 7 is an amino acid length representing a spacer, wherein the 'X+7' is configured to bind a Fc fragment and a fifth site wherein a nanoparticle coated with at least one of a cationic, anionic or zwitterionic ligand. Further yet, a half-life optimized linker (H-Lo) further comprises of a fifth site configured for facilitating encapsulation by a carrier of the linker with RBD. Further yet, the carrier is a nanoparticle of a size between 30 nm and 100 nm.

In one embodiment, the H-Lo linker is an 'X+7' chain, serving as the sole intermediary between the RBD and the LED. In other embodiments, the H-Lo linker is further attached to an additional amino acid sequence intermediating between the RBD and LED. The presence and extent of the amino acid sequence intermediating, along with the H-Lo linker, may depend on at least one of the RBD target site, RBD-H-Lo Linker structural conformation, LED-H-Lo structural conformation, or RBD-H-Lo-LED structural conformation. In other embodiments, at least one of the H-Lo linkers or intermediary a.a sequences bridging the RBD and LED may be further linked by disulfide bonds. The number or extent of disulfide bonds and their relative bonding strength may depend on at least one of the RBD target site, RBD-H-Lo Linker structural conformation, LED-H-Lo structural conformation, or RBD-H-Lo-LED structural conformation.

Any one of the LED's described, or combination of LED's may be fused depending on at least one of the RBD target site, RBD-H-Lo Linker structural conformation, LED-H-Lo structural conformation, or RBD-H-Lo-LED structural conformation. Furthermore, any one of or combination of LED's may have additional therapeutic value apart from serving as a half-life extending domain. For instance, it has been clinically demonstrated that Albumin may facilitate in the antagonism of the ACE-2 receptor, in addition to half-life extending the RBD—effectively compounding the efficacy value of the Sars-CoV-2 RBD. Other therapeutic values apart from enhancing receptor antagonism and half-life extension may be viable for any one of, or combination of, LED domains or RBD-LED complexes.

Screening and selection of preferred immunoglobulins (antibodies) can be conducted by a variety of methods known to the art. Initial screening for the presence of monoclonal antibodies specific to a target receptor may be conducted through the use of ELISA-based methods or phage display, for example. A secondary screen is preferably conducted to identify and select a desired monoclonal antibody for use in construction of the fusion polypeptides of the invention. Secondary screening may be conducted with any suitable method known to the art.

Individual components of the fusion polypeptides of the invention may be produced from nucleic acids molecules using molecular biological methods known to the art. Nucleic acid molecules are inserted into a vector that is able to express the fusion polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional/translational control signals. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Fully human antibodies may be made by any method known to the art. For example, U.S. Pat. No. 6,596,541 describes a method of generating fully human antibodies.

In accordance with the invention, the nucleic acid constructs include components which encode binding domains derived from target receptor ligands. After identification of a ligand's target receptor-binding domain exhibiting desired binding characteristics, the nucleic acid that encodes such domain is used in the nucleic acid constructs. Such nucleic acids may be modified, including additions of nucleotide sequences encoding amino acids and/or carrying restriction sites, deletions of nucleotide sequences encoding amino acids, or substitutions of nucleotide sequences encoding amino acids.

The nucleic acid constructs of the invention are inserted into an expression vector or viral vector by methods known to the art, wherein the nucleic acid molecule is operatively linked to an expression control sequence. Also provided is a host-vector system for the production of the fusion polypeptides and activating dimers of the invention, which comprises the expression vector of the invention, which has been introduced into a suitable host cell. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

Methods of introduction of the novel fusion antibody can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

With respect to fusing Albumin as the Half-Life Extending Domain (LED), there are a number of purification methods, ranging from Plasma fractionation using ethyl alcohol, Cohn method, placenta purification, affinity precipitation, heat shock, and ammonium sulfate precipitation with liquid chromatography. Other methods include ion exchange chromatography, steric exclusion chromatography, expanded bed adsorption chromatography, simulated moving bed chromatography, and affinity chromatography methods.

Human serum albumin and the desired RBD may be later expressed by either stable or transient transfection on a chosen cell line. They are purified using various protein purification methods and processed further as necessary. This has been demonstrated on Lys64 of HSA for trastuzumab, but can be used for other monoclonal antibodies. The expressions of the trastuzumab fusions were located at the N-terminus of the light chain or the C-terminal of the heavy chain. This allowed conjugation of small molecules. The HAS domains were amplified by PCR from a full length HSA gene. Trastuzumab heavy and light chains were modified to have leader sequences and ligated into the designated restriction sites to produce the Fc-HSAdIC34S vector. HEK cells were used as a cell line.

With respect to fusing with or encapsulating a nanoparticle as a means to extend the half-life of the construct (RBD), standard techniques range from desolvation, emulsification, thermal gelation, nanospray drying, nano albumin bound technology and self-assembly.

One protocol for half-life extending uses PEG 3400-DSPE conjugation to an anti-target X antibody, involves adding 2 mg of DSPE-$PEG_{3400}$-NHS to this anti-target X antibody solution of 1 mg/1 mL in PBS. At room temperature, this mixture is then subsequently stirred for an estimated 4 hours. For quenching, an excess of 5 mg of glycine can be used. Subsequently, a micelle solution can be produced and further purified by a Sepharose CL 4B with a PBS buffer at pH 7.2 in a setting that has a mobile phase. A target X mixed micelle can prepared from lipid compositions of an anti-target X antibody conjugated to $PEG_{3400}$-DPSE and $mPEG_{2000}$DPSE with a typical a desired weight ratio which is typically 1:3. Target X is then mixed with $PEG_{3400}$DSPE micelles. This would have produced a result of an estimated 2 mg lipid in 0.5 mL PBS which is incubated with 2 mg of a designated drug compound for 4 hours at 60 C in a water bath stirred continuously. Chromatography on Sepharose CL-4B columns can be used for further separation. Methoxypoly(ethylene glycol) (Mw 2000 Da), covalently linked to distearoyphosphadidylethanoloamine ($mPEG_{2000}$-DSPE) 1,2-Distearoyl-sn-glycero-3-phosphoethanolamine-N-[succinimidyl (polyethylene glycol)] (DSPE-$PEG_{3400}$-NHS)

This involves a protocol can involve various NP materials, sizes as well as surface ligands. NP can be attached with electrostatic interactions. For example, a protein having a positive net charge can attach to a citrate NP, which has a negative charge. The NP and protein solutions need to be mixed in a conjugation buffer with a targeted nanoparticle with protein molar incubation ratio. Gold NP of 1.5 nm, for example, typically use an estimated 0.1 mM, thereby allowing proper visualization of the gel. Poly(ethylene glycol) thiol, for example, with gold nanoparticles can help prevent undesired protein folding. The solution is then incubated at 4 C overnight.

The designated gene sequence contains entire length of the fragments. VHH fragments as noted elsewhere are replaced for RBD (which can and can be without the spacer), linkers and the humanized FC component containing IgG2 or even IgG1. Evaluation involves compliment codon optimization to scale expression of the desired antibody. Sequence cloning of designated areas are used to generate an expression plasmid. Expression is done by transfection of cell line such as HEK 293. This may involve transient or stable transfection. A stepwise purification process with quality control allows the final component process. Further analysis for protein production and purification can utilize sodium dodecyl sulfate (SDS)-polyacrylamide gel electrophoresis (SDS-PAGE). This can be done using 12 or 15% (with/volume) SDS-gels, with subsequent staining, such as Coomassie staining. Testing of binding can implement the ACE-2 receptor to quantify ACE-2-RBD containing antibody. Surface plasma resonance or binding octet are additional binding evaluations.

While this specification contains many specific execution details, these should not be interpreted as limitations on the scope of any inventions or of what may be claimed, but rather as descriptions of features specific to particular embodiments of particular inventions. Certain features that are described in this specification in the context of separate embodiments can also be implemented in combination in a single embodiment. Contrariwise, various features that are described in the context of a single embodiment can also be implemented and interpreted in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub combination. Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

I claim:

1. A composition comprising a half-like optimized fusion protein linked by a Half-Life Optimizing (H-Lo) linker, said composition comprising:
   a receptor binding domain (RBD) of a SARS CoV-2 virus;
   a half-life extending domain (LED), wherein the LED is a Fc fragment of a humanized Camelid IgG monoclonal antibody; and
   the H-Lo linker with an (X+7 amino acid) length fusing a C-terminus of said RBD with an N-terminus of said LED (RBD-LED fusion), wherein a value for said x varies depending on a structural conformation of an interacted RBD-LED fusion and wherein the 7 is the number of amino acids representing a spacer portion of the H-Lo linker and consists of the amino acids TES-IVRF (SEQ ID NO: 1).

2. The composition of claim 1, wherein the RBD of the SARS CoV-2 virus is S (spike) protein.

3. The composition of claim 2, wherein the S protein further comprises a S1 and a S2 subunit.

4. The composition of claim 1, wherein the RBD-LED fusion is recombinantly engineered by phage display/yeast display technologies.

5. The composition of claim 1, wherein the H-Lo linker is between 2 and 31 amino acids in length.

6. The composition of claim 1, wherein the H-Lo linker further comprises at least one of Glycine, Serine or Threonine.

7. The composition of claim 1, wherein the value for X further depends on the construction of a functional chimeric protein.

8. The composition of claim 7, wherein the value for X is at least in a range of 5-11 amino acids.

9. The composition of claim 1, wherein the RBD-LED fusion is half-life optimized for prolonged targeting of an ACE-2 receptor for antagonist binding.

10. The composition of claim 9, wherein the ACE-2 receptor antagonism results in a failure of a SARS-COVID-2 spike protein binding and a subsequent SARC-COVID-2 viral infection.

11. The composition of claim 1, wherein the ACE-2 RBD-Camelid Fc LED fusion with H-Lo linker is deliverable of intravenously, subcutaneously, nasally, or orally.

12. The composition of claim 1, wherein the LED further comprises albumin.

13. The composition of claim 12, wherein the albumin further comprises a functional value apart from half-life extending the RBD.

14. The composition of claim 13, wherein the functional value is facilitating ACE-2 receptor antagonism.

15. The composition of claim 1, wherein the X+7 linker is further attached to a spacer.

* * * * *